United States Patent
Bacon et al.

(10) Patent No.: US 7,544,517 B2
(45) Date of Patent: Jun. 9, 2009

(54) STABILIZED REAGENT, APPARATUS AND METHOD FOR MEASURING CYANURIC ACID

(75) Inventors: Steven M. Bacon, Sparks, MD (US); Jimmie L. P. Melton, Sparks, MD (US); Indranee C. Kuruppunayake, Sparks, MD (US)

(73) Assignee: Taylor Technologies, Inc., Sparks, MD (US)

( * ) Notice: Subject to any disclaimer, the term of this patent is extended or adjusted under 35 U.S.C. 154(b) by 780 days.

(21) Appl. No.: 11/281,781

(22) Filed: Nov. 16, 2005

(65) Prior Publication Data

US 2006/0084179 A1    Apr. 20, 2006

Related U.S. Application Data

(63) Continuation-in-part of application No. 10/735,453, filed on Dec. 11, 2003, now Pat. No. 7,326,383.

(51) Int. Cl.
*G01N 21/77* (2006.01)

(52) U.S. Cl. .................. 436/169; 436/164; 436/166; 422/55; 422/56; 422/57

(58) Field of Classification Search .................. None
See application file for complete search history.

(56) References Cited

U.S. PATENT DOCUMENTS

| | | | |
|---|---|---|---|
| 4,129,417 | A | 12/1978 | White |
| 4,855,239 | A | 8/1989 | Rupe |
| 5,710,372 | A | 1/1998 | Becket |
| 6,413,473 | B1 | 7/2002 | Bacon |
| 6,432,717 | B1 | 8/2002 | Fernando |
| 2003/0147777 | A1 | 8/2003 | Ghanekar |

*Primary Examiner*—Yelena G Gakh
(74) *Attorney, Agent, or Firm*—Fulbright & Jaworski LLP

(57) ABSTRACT

Reagents for determining presence or concentration of cyanuric acid are described. The reagents include an indicator, a 2,4-diamino-6-alkyl-1,3,5-triazine, caffeine, which acts as a stabilizer, and may include an antioxidant.

13 Claims, No Drawings

STABILIZED REAGENT, APPARATUS AND METHOD FOR MEASURING CYANURIC ACID

RELATED APPLICATION

This application is a continuation in part of application Ser. No. 10/735,453 filed Dec. 11, 2003 now U.S. Pat. No. 7,326,383, incorporated by reference in its entirety.

FIELD OF THE INVENTION

This invention relates to apparatus, methods, and reagents useful in analyzing liquid samples. More particularly, the invention relates to analyzing liquid samples to determine cyanuric acid in such a liquid sample.

BACKGROUND AND PRIOR ART

The science of analytical chemistry has, and continues to make progress. The field involves the ability to assay sample materials to determine if a particular substance or substances are present, and if so, the amount of that substance. Frequently, the term "analyte" is used to describe the substance being tested. This term will be used hereafter.

Early examples of the application of analytical chemistry include litmus paper, as well as devices which would change color if atmospheric humidity was above a particular level. To say that the field has become more sophisticated since then is an understatement.

One area of importance in analytical chemistry is the testing and evaluation of liquid samples. While "liquid sample" as used hereafter refers to materials such as blood, urine, but most particularly for this disclosure, water.

It is desirable and necessary to analyze water for various components. For example, it may be important to determine if a water sample is potable. Further, water samples are used for different purposes. Depending upon the use to which the sample is to be put, one or more parameters, such as pH, total alkalinity, calcium hardness, total hardness, and amount of particular analytes such as total chlorine, free chlorine, combined chlorine, sodium content, etc., may be important. For example, when the Water sample is taken from a swimming pool, either or both of combined chlorine and free chlorine may be important. Where the water is to be used for an industrial cooling system, total alkalinity or total hardness may be important. When the water is to be used in the health profession, any number of analytes may be of interest and important. These are just examples of the type of uses to which water samples may be put. The skilled artisan will be familiar with many others, which need not be set forth here. Further, the literature on analysis of liquid samples other than water is vast.

Analysis of water samples can be accomplished with any number of different systems. Generally, however, these systems can be divided into "dry chemistry" and "wet chemistry" systems.

In a wet chemistry system, essentially one adds either a liquid testing agent or a dissolvable testing agent to a liquid sample. The testing agent reacts with the analyte of interest, leading to formation of a detectable signal. Preferably, this is the formation of a visible "marker," such as a color or change in color. Again, the artisan will be familiar with other systems such as measurement of light absorption in photometers, etc. For purposes of this disclosure, however, the discussion will focus on visible formation and changes in color, rather than systems such as light photometers solely to facilitate understanding.

In these wet chemistry systems, the reacted liquid sample is then compared to some reference standard. Generally, this takes the form of a coded reference linking concentration of the analyte to a particular color or degree of color. A low concentration may be indicated by a very pale pink color, and a high concentration by one which is dark red, and vice versa.

Dry chemistry systems can be used to analyze many of the types of samples that wet chemistry systems are used to analyze. In these dry chemistry systems an apparatus, such as an absorbent pad or a test strip is impregnated, coated, or printed with the test system discussed supra, in such a way that the test system does not and cannot leave the apparatus. The apparatus is contacted with the liquid sample, removed from it, and the signal is "read" on the apparatus. As with wet chemistry systems, the signal that is generated is compared to a coded reference to link the signal generated to a specific amount and/or concentration of an analyte under consideration.

The prior art literature on analytical chemistry is vast. For example, U.S. Pat. No. 5,811,254, to Wu, teaches reagent systems which can be used to detect total available chlorine over an extensive range (0 to 5000 ppm). The reagents can be incorporated into a carrier matrix, such as filter paper, to produce a dry chemistry test strip useful in measuring total available chlorine. U.S. Pat. No. 5,710,372, to Becket, teaches test strips which include a plurality of test regions. Each region contains a different amount of a reagent system which reacts with an analyte of interest. A visual display results which permits the user to determine the amount of the analyte in the sample being analyzed. U.S. Pat. No. 5,620,658, to Jaunakais, teaches multicomponent test strips which contain reagents capable of converting undetectable analytes into detectable ones, via ionic change. U.S. Pat. No. 5,529,751, to Gargas, teaches a pH adjustment kit. Once the pH of the sample has been determined, a first reagent is added until the sample indicates that a proper pH has been obtained. The number of drops of the first reagent is then converted to a quantity of a second reagent, which is then used to modify pH of the source of the sample. U.S. Pat. No. 5,491,094, to Ramana, et al., teaches dry reagent test strips for determining free chlorine, using TMB derivatives. U.S. Pat. No. 4,904,605, to O'Brien, et al., teaches test strips which can be used to determine a plurality of different reagents. A dipstick containing a plurality of reagent pads is contacted to sample, signal is formed, and then compared to a reference standard. U.S. Pat. No. 4,481,296, to Halley, teaches compositions that are useful in determining the pH of a halogen containing solution.

As the number of swimming pools and spas increases, the need for effective tools to monitor and control pool water chemistry and especially sanitizer levels becomes more and more important. This is especially true in pools used by the public where the bather concentration is high and the threat of contagious diseases is always present. In order to control the harmful microorganism population of pools, it has been found over the years that chlorine is the most effective and economical sanitizer. However, as popular as chlorine is, it nevertheless has certain drawbacks which must be considered. A particularly serious problem associated with the use of chlorine in outdoor pools is that it tends to be destroyed by sunlight.

In this regard it has been found that the addition of cyanuric acid (2,4,6-trihydroxy-1,3,5-triazine) to pool water can be effective as an extender or stabilizer for chlorine. However, the concentration must be rather carefully adjusted since too little obviously is ineffective as a stabilizer for the chlorine while too much can dramatically slow down the rate at which microorganisms are destroyed by the chlorine. It has been found that the effective concentration of cyanuric acid lies between 30 and 100 parts per million (ppm).

In order to maintain the effectiveness of the cyanuric acid in the swimming pool, it is necessary to measure the concentration thereof using a test device or concentration measuring system. The current test most commonly used in the swimming pool industry involves the melamine turbidimetric method. In this scheme, melamine is added to a sample of the pool water which, in the presence of cyanuric acid, causes the formation of a finely dispersed precipitate. The turbidity created by this precipitate formation is proportional to the amount of cyanuric acid present. By measuring this turbidity using visual or instrumental schemes, an estimation of the concentration of cyanuric acid can be obtained. This test however is not completely acceptable since turbidimetric methods tend, in general, to be unreliable in that other factors can cause turbidity and precipitates are obviously less homogenous than solutions.

For this reason, attempts have been made over the years to replace the turbidimetric analytical procedures with calorimetric methodologies.

Various approaches have been suggested for determining cyanuric acid in samples. For example, U.S. Pat. No. 2,986,452 to Merek suggests the addition of sodium acetate and a soluble copper salt. Mancini, U.S. Pat. No. 4,039,284, utilized a combination of thymolsulfonphthalein and monoethanolamine.

With Stillman, U.S. Pat. No. 4,793,935, more modern systems can be seen. This patent teaches that cyanuric acid, when reacted with melamine, forms a precipitate thus removing the cyanuric acid from water. It is not an analytical method.

U.S. Pat. No. 4,855,239 to Rupe uses melamine as a component of an indicator system for determining cyanuric acid, and Fernando, U.S. Pat. No. 6,432,717, involves an improvement on this earlier patent using a stabilizing compound. Ghanekar, published Application U.S. 2003/0147777, uses an indicator which changes color in response to a change in pH as a way to determine cyanuric acid.

Melamine is somewhat structurally related to the compound acetoguanamine, or 2,4-diamino-6-methyl-1,3,5-triazine, differing in that melamine has an amino group at position 6, whereas acetoguanamine has a methyl group.

While there is this element of structural similarity, it has been found that, among compounds structurally related to melamine, the 6-alkyl derivatives, acetoguanamine, in particular, are useful in cyanuric acid assays, as will be shown in the disclosure which follows.

DETAILED DESCRIPTION OF PREFERRED EMBODIMENTS

Example 1

The feasibility of using 2,4-diamino-6-methyl-1,3,5-triazine ("DAMT" hereafter) was tested in solution based assays.

A stock solution of cyanuric acid (2000 ppm) was prepared and then diluted to 40, 100, 200, and 300 ppm. A reagent blank with 0 ppm cyanuric acid ("CYA" hereafter) was also used. The pH of each solution was adjusted with 0.1N HCl to 6.8 and the indicator phenol red was added. DAMT was then added, and any color changes were monitored visually.

Gradations from yellow (0 ppm CYA) to reddish purple (300 ppm CYA) were observed, suggesting that DAMT could be used to differentiate CYA levels.

Example 2

The results, supra, suggested testing phenol red, as well as the indicator cresol red in dry paper test strips.

Formulations of DAMT in deionized water (1%) were prepared.

Indicator dips were prepared by mixing 8.0 ml of a 0.5% solution of the sodium salt of one of the indicators mentioned supra, 67.5 ml (0.675%) of the DAMT solution, and 24.5 ml of deionized water. The solution of phenol red was adjusted to pH 6.8, and that of cresol red, to pH 7.2.

Each solution was then used to impregnate a variety of filter papers, which were then dried, at 90° C., and tested in CYA solutions, prepared from the stock standard CYA solution, as discussed supra, with the exception that the pH of the standard solution was adjusted to 7.5, and the pH of test solutions was not adjusted.

Several of the test strips gave good results, with clear color demarcations at the different CYA concentrations.

In an attempt to improve the product, the experiments described supra were repeated, with the pH adjusted up to 7.5 for cresol red, and 7.2 for phenol red.

All tests gave good results.

Example 3

The impact the pH of a solution had on the test was studied, by adjusting the pH of the 0 ppm CYA solution to about 7, and about 8. The dipsticks, as described supra, were tested, and compared to the first set of results.

Phenol red strips, when dipped in the 0 ppm standard at 7.0, gave a false positive reading of about 70 ppm CYA, and about 100 ppm when dipped in the 0 ppm standard, at pH 8. Cresol red strips gave results comparable to about 60 and 80 ppm, respectively.

These results suggested that it would be desirable to modify the strips slightly to avoid false positives.

Example 4

A reagent solution was prepared by combining 5 ml 0.4% cresol red sodium salt, 50 ml 1.3% DAMT, and adjusting it to a pH 7.4 with 0.1N HCl. A strip of paper (1.5"×6") was immersed in the solution and excess liquid was removed with a stirring rod. The end was touched off on an absorbent towel. The paper was dried for 30 minutes at 60° C. The dried paper was attached to 3M double stick tape, one/fifth inch of the edges was discarded, and cut into ⅕ inch strips. The backing was peeled off and the paper with double stick tape was mounted on a plastic card near the long edge, and the card was cut into ⅕ inch test strips.

Test solutions were prepared by adjusting tap water with sodium bicarbonate to give an alkalinity of 100 ppm, then a 2000 ppm cyanuric acid solution was diluted with the 100 ppm water to give cyanuric acid solutions of 0, 50, 100, 200, and 300 ppm cyanuric acid. The pH of each solution was adjusted to 7.4 with 0.1N HCl.

The cyanuric acid solutions were then tested with the above test strips. The test strips gave easily distinguishable colors ranging from tan-yellow to red purple. All levels were easily distinguishable from adjacent levels.

Example 5

Test strips were prepared as in example 1, except 2,4-diamino-6-methyl-1,3,5-triazine was replaced by 0.6% 2,4-diamino-6-n-butyl-s-triazine. The test strips were tested as in Example 4. The range of color was not as large as in example one, but adjacent levels could be distinguished.

Example 6

The example describes the manufacture of cyanuric acid determining dipsticks, as optimized.

| A formulation (1 liter) was mixed which contained: | |
|---|---|
| Cresol red, sodium salt | 0.5 g |
| DAMT | 12.0 g |
| Sodium thiosulfate, 5H$_2$O | 0.5 g |
| Propylene glycol | 40 ml |
| Deionized water | 960 ml |

The pH of the solution was 6.9. The sodium thiosulfate is an antioxidant which inhibits halogenation from, e.g., chlorine when a halide or halogen is present in the test sample. The propylene glycol acts to stabilize the mixture and to facilitate even application to the paper. Using this formula, the test paper was impregnated, and dried.

Strips thus prepared were tested with CYA standards adjusted to 100 ppm total alkalinity, as described supra, and showed color differentiation at different concentrations.

Example 7

The compound ethylenebismelamine, described in U.S. Pat. No. 5,514,213, incorporated by reference, was tested as described, supra, and also showed differentiation at varying concentrations.

The foregoing examples describe the features of the invention, which relate to the use of 2,4-diamino-6-alkyl-1,3,5-triazines in the preparation of reagents and apparatus useful in determining concentrations of cyanuric acid in fluids, such as liquids, including water, such as swimming pool water, sauna or spa water, and so forth. The alkylene moiety in these compounds may be straight or branched, substituted or unsubstituted, and contain from 1 to 10 carbon atoms, more preferably 1 to 6 carbon atoms, and is most preferably straight chained, unsubstituted, containing from 1 to 4 carbon atoms.

The compound described supra is combined with an indicator molecule, and may optionally contain a substance, which inhibits interference by other analytes, such as an antioxidant which inhibits halogenation, and/or a stabilizer. Exemplary of indicators are cresol red, phenol red, thymol blue, m-cresol purple, or any of the other indicators well known in the art, which exhibit a visible color change or formation of color at the pH range. Further examples include nitrazine yellow, bromothymol blue, bromophenol blue, brilliant yellow, neutral red, 3-nitrophenol, orange II, phenolbenzein (aurin), cresolbenzien, and other indicators well known to the artisan. The interference inhibitor may be an antioxidant such as sodium thiosulfate, sodium metabisulfite, sodium bisulfite, sodium sulfite, ascorbic acid, 3-tert-butyl-4-hydroxyanisole, 2,6-di-tert-butyl-4-methylphenol or other antioxidants well known in the art. The stabilizer is preferably propylene glycol, but the skilled artisan will be aware of other useful stabilizers, such as ethylene glycol, other alkylene glycols, and so forth.

The reagent is formulated so as to have a pH of from about 6.0 to about 9.0, more preferably from about 6.5 to about 8.0, and most preferably, from about 6.5 to about 7.5. The reagents may be in liquid form, or as a combination of dry ingredients, or may be formulated as kits, wherein a container means affords a holding device for the components, which are kept separate from each other until used by the artisan.

The reagents may be applied to a solid substrate, such as a bibulous paper, or other absorbent or absorbent medium, and then dried, so that they can be used, e.g., as dipsticks to analyze cyanuric acid content of samples. One may use oxygenated solvents, like MEK or MIBK to increase solubility of the triazine and permit deposition of more reagent thereon.

Solid substrates containing the reagent of the invention may be formulated so that the apparatus contains only the reagent described supra, or may be a component of a solid substrate which measures other parameters as well.

The terms and expression which have been employed are used as terms of description and not of limitation, and there is no intention in the use of such terms and expression of excluding any equivalents of the features shown and described or portions thereof, it being recognized that various modifications are possible within the scope of the invention.

Example 8

The example describes the manufacture of cyanuric acid determining dipsticks, as optimized.

| A formulation (1 liter) was mixed which contained: | |
|---|---|
| Cresol red, sodium salt | 0.6 g |
| DAMT | 20.0 g |
| 3,7-dihydro-1,3,7-trimethyl-1H-purine-2,6-dione (caffeine) | 20.0 g |
| Sodium thiosulfate, 5H$_2$O | 0.5 g |
| Methanol | 200 ml |
| Deionized water | 800 ml |

The pH of the solution was 7.0. The sodium thiosulfate is an antioxidant which inhibits halogenation from, e.g., chlorine when a halide or halogen is present in the test sample. The caffeine acts to stabilize the mixture and to facilitate even application to the paper. Using this formula, the test paper was impregnated, and dried.

Strips thus prepared were tested with CYA standards adjusted to 100 ppm total alkalinity, as described supra, and showed color differentiation at different concentrations.

Example 9

The compound ethylenebismelamine, described in U.S. Pat. No. 5,514,213, incorporated by reference, was tested as described, supra, and also showed differentiation at varying concentrations.

The foregoing examples describe the features of the invention, which relate to the use of 2,4-diamino-6-alkyl-1,3,5-triazines, such as DAMT, in the preparation of reagents and apparatus useful in determining concentrations of cyanuric acid in fluids, such as liquids, including water, such as swimming pool water, sauna or spa water, and so forth. The alkylene moiety in these compounds may be straight or branched, substituted or unsubstituted, and contain from 1 to 10 carbon atoms, more preferably 1 to 6 carbon atoms, and is most preferably straight chained, unsubstituted, containing from 1 to 4 carbon atoms.

The compound described supra is combined with an indicator molecule, and may optionally contain a substance, which inhibits interference by other analytes, such as an antioxidant which inhibits halogenation, and/or a stabilizer. Exemplary of indicators are cresol red, phenol red, thymol blue, m-cresol purple, or any of the other indicators well known in the art, which exhibit a visible color change or formation of color at the pH range. Further examples include nitrazine yellow, bromothymol blue, bromophenol blue, brilliant yellow, neutral red, 3-nitrophenol, orange II, phenolbenzein (aurin), cresolbenzien, and other indicators well known to the artisan. The interference inhibitor may be an antioxidant such as sodium thiosulfate, sodium metabisulfite, sodium bisulfite, sodium sulfite, ascorbic acid, 3-tert-butyl-4-hydroxyanisole, 2,6-di-tert-butyl-4-methylphenol or other antioxidants well known in the art. The stabilizer is preferably caffeine, but the skilled artisan will be aware of other useful stabilizers, such as propylene glycol, polyvinyl pyrrolidone, polyacrylate, other polymers and co-polymers, and so forth.

The reagent is formulated so as to have a pH of from about 6.0 to about 9.0, more preferably from about 6.5 to about 8.0, even more preferably, from about 6.5 to about 7.5, and most preferably, about 7.0. The reagents may be in liquid form, or as a combination of dry ingredients, or may be formulated as kits, wherein a container means affords a holding device for the components, which are kept separate from each other until used by the artisan.

The reagents may be applied to a solid substrate, such as a bibulous paper, or other absorbent or absorbent medium, and then dried, so that they can be used, e.g., as dipsticks to analyze cyanuric acid content of samples. One may use oxygenated solvents, like MEK or MIBK to increase solubility of the triazine and permit deposition of more reagent thereon.

Solid substrates containing the reagent of the invention may be formulated so that the apparatus contains only the reagent described supra, or may be a component of a solid substrate which measures other parameters as well.

The terms and expression which have been employed are used as terms of description and not of limitation, and there is no intention in the use of such terms and expression of excluding any equivalents of the features shown and described or portions thereof, it being recognized that various modifications are possible within the scope of the invention.

The invention claimed is:

1. Stabilized reagent useful in determining cyanuric acid in a fluid sample, comprising (i) a 2,4-diamino-6-alkyl-1,3,5-triazine or ethylenebismelamine, wherein said alkyl contains from 1 to 10 carbons, is straight chained or branched, substituted or unsubstituted, (ii) an indicator molecule, and (iii) 3,7-dihydro-1,3,7-trimethyl-1H-purine-2,6-dione ("caffeine") wherein said stabilized reagent is at a pH of from about 6 to about 9.

2. The reagent of claim 1, wherein said reagent is at a pH of from about 7.0 to about 9.

3. The reagent of claim 1, further comprising an antioxidant.

4. The reagent of claim 1, wherein said alkyl is straight chained and consists of 1 to 4 carbon atoms.

5. The reagent of claim 1, wherein said reagent comprises 2,4-diamino-6-methyl-1,3,5-triazine.

6. The reagent of claim 1, wherein said indicator is cresol red or phenol red.

7. The reagent of claim 3, wherein said antioxidant is sodium thiosulfate.

8. The reagent of claim 3, comprising cresol red, 2,4-diamino-6-methyl-1,3,5-triazine, caffeine, and sodium thiosulfate.

9. Apparatus comprising the reagent of claim 1, impregnated, absorbed or absorbed onto a solid carrier.

10. The apparatus of claim 9, wherein said solid carrier is absorbent or absorbent paper.

11. The apparatus of claim 10, further comprising at least one other reagent suitable for determining a second analyte.

12. A method for determining cyanuric acid in a fluid sample, comprising contacting said sample with the reagent of claim 1 and determining formation of or change of a color as an indication of presence or concentration of cyanuric acid in said fluid sample.

13. The method of claim 12, wherein said fluid sample is swimming pool water.

* * * * *